(12) United States Patent
Darrow et al.

(10) Patent No.: US 10,933,516 B2
(45) Date of Patent: Mar. 2, 2021

(54) SCHANZ SCREW WRENCH COMBINATION TOOL

(71) Applicant: DePuy Synthes Products, Inc., Raynham, MA (US)

(72) Inventors: Jeffrey Darrow, West Chester, PA (US); Steven Krevitski, West Chester, PA (US); Kory Smith, West Chester, PA (US); Robert Mazzarello, West Chester, PA (US); Donald Lu, West Chester, PA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 317 days.

(21) Appl. No.: 16/178,130

(22) Filed: Nov. 1, 2018

(65) Prior Publication Data

US 2020/0139517 A1  May 7, 2020

(51) Int. Cl.
*B25B 13/56* (2006.01)
*B25G 1/10* (2006.01)
*B25B 23/16* (2006.01)
*B25B 13/06* (2006.01)

(52) U.S. Cl.
CPC .............. *B25B 13/56* (2013.01); *B25B 13/06* (2013.01); *B25B 23/16* (2013.01); *B25G 1/102* (2013.01)

(58) Field of Classification Search
CPC ......... B25B 13/56; B25B 13/06; B25B 23/16; B25G 1/102; B25G 1/105; A61B 17/8875; A61B 17/8877; A61B 17/8883; A61B 17/8886
See application file for complete search history.

(56) References Cited

U.S. PATENT DOCUMENTS 5,507,211 A * 4/1996 Wagner .............. A61B 17/8875
81/125

* cited by examiner

*Primary Examiner* — David B. Thomas
(74) *Attorney, Agent, or Firm* — Fay Kaplun & Marcin, LLP

(57) ABSTRACT

A wrench device includes a proximal member including a first recess and a second recess open to the first recess. The second recess has a width smaller than the first recess. The first recess receives a first screw and the second recess receives a second screw smaller in diameter than the first screw. The device also includes a distal member coupled to the proximal member. The distal member includes a first recess, a second recess open to the first recess, and a third recess open to the second. The first recess has a width larger than a diameter of the second recess. The second recess has a diameter larger than the third recess. When the proximal and distal members are coupled, the first and second recesses of the proximal member are in open communication with the first, second and third recesses of the distal member.

18 Claims, 5 Drawing Sheets

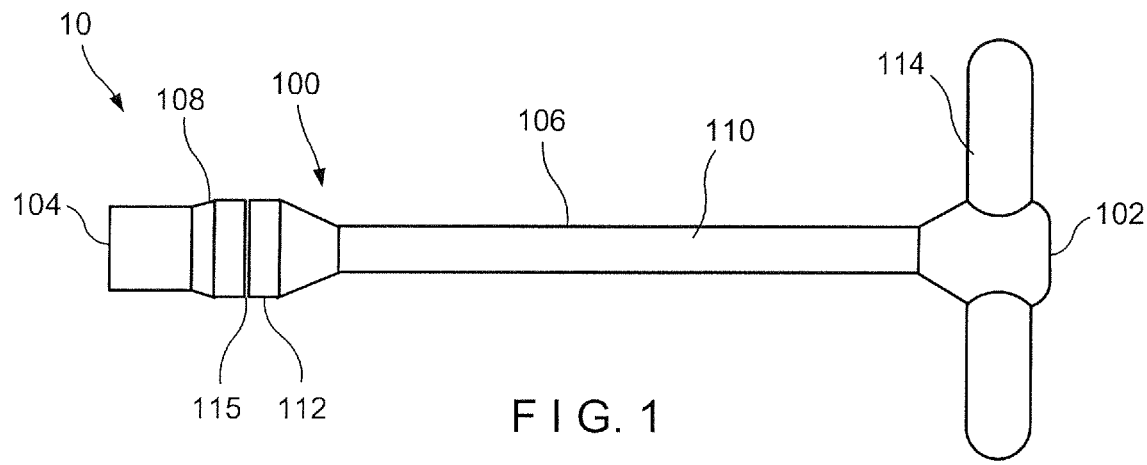
F I G. 1
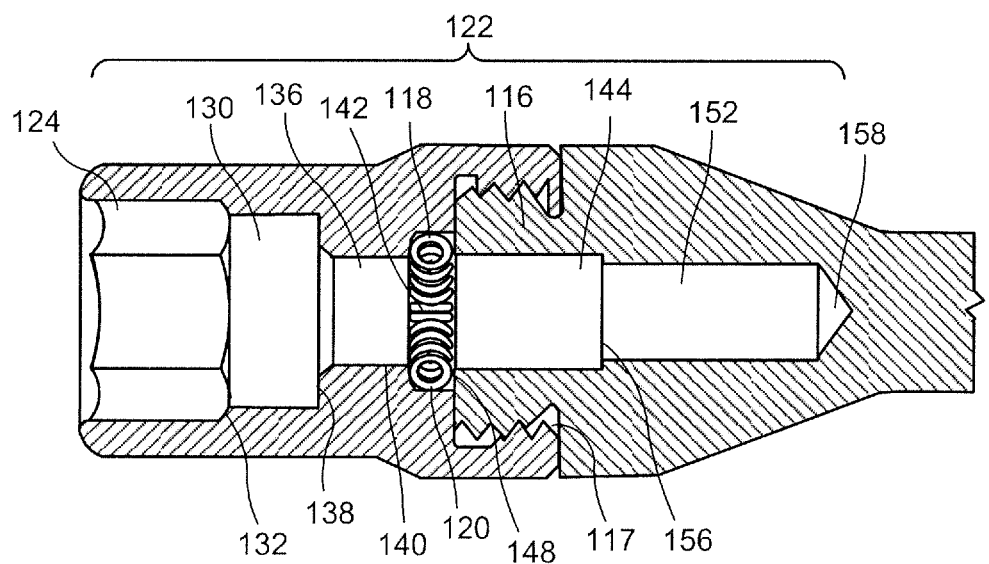
F I G. 2
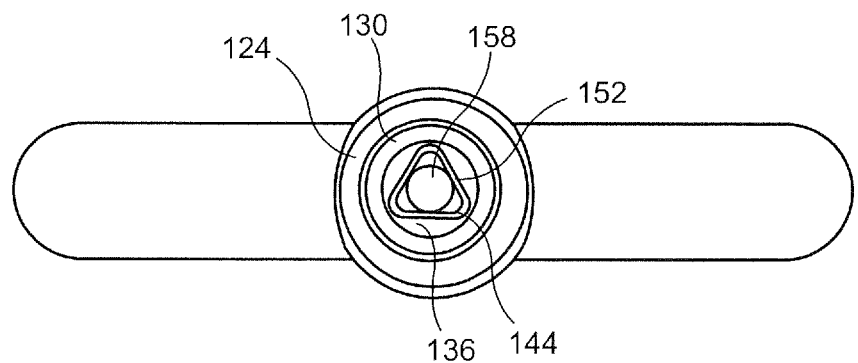
F I G. 3

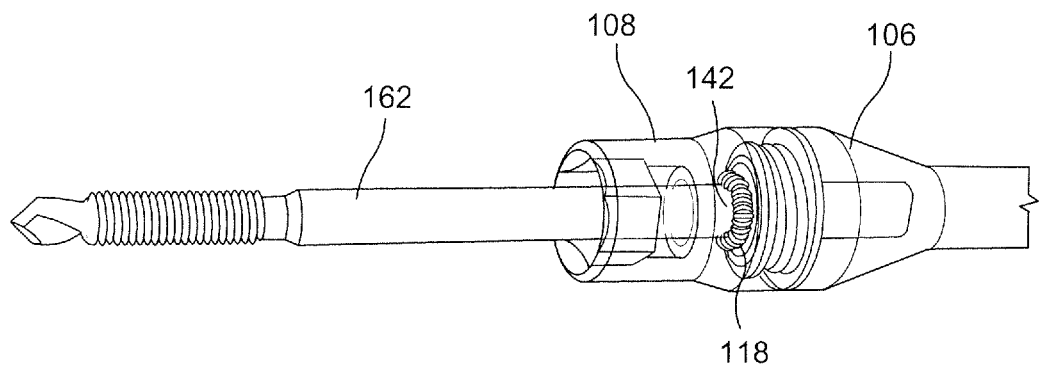
F I G. 7
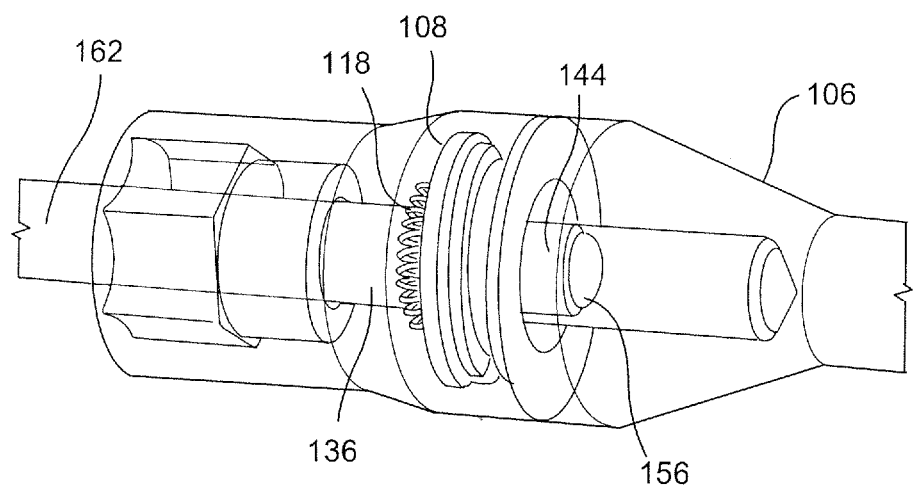
F I G. 8

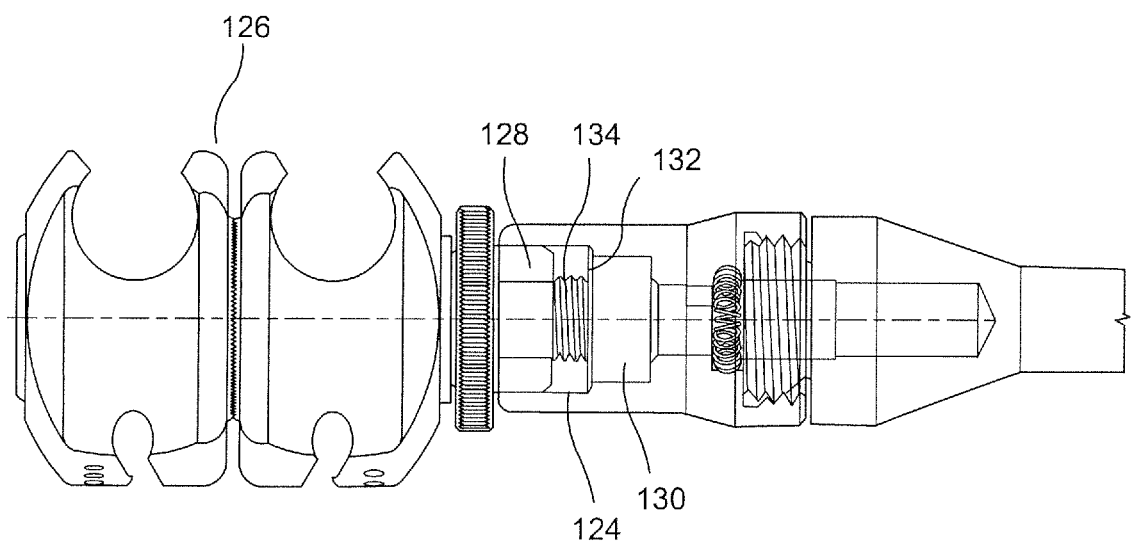
F I G. 9
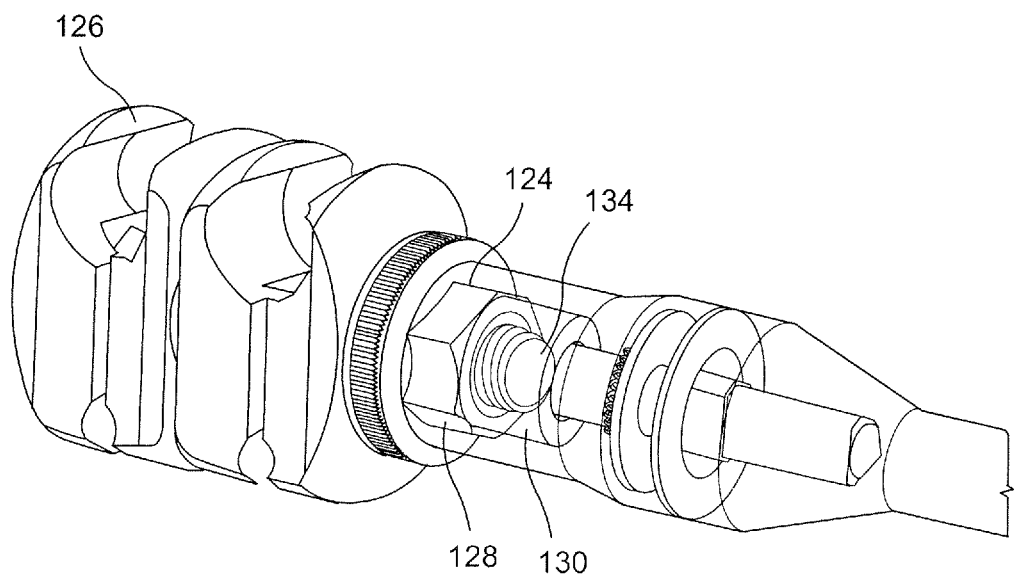
F I G. 10

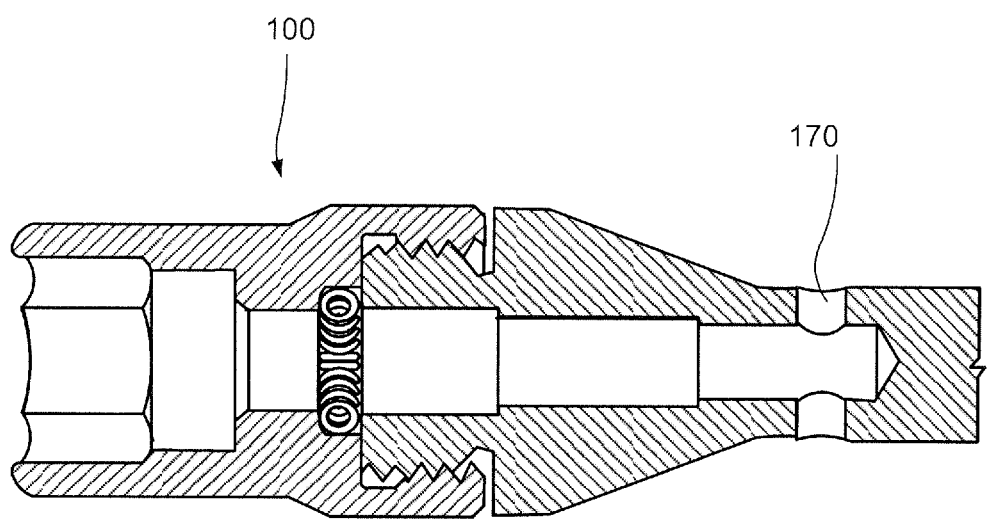
F I G. 11

SCHANZ SCREW WRENCH COMBINATION TOOL

FIELD

Aspects of the present disclosure relate generally to medical tools. Particular aspects relate generally to wrench tools for adjusting Schanz screws and tightening nuts.

BACKGROUND

Procedures involving external fixation systems often use multiple tools for adjusting different sized Schanz screws, as well as tightening nuts on combination clamps. For example, existing instruments must be manually adjusted to the different sized Schanz screws and a separate tool must be used for tightening nuts.

SUMMARY

The present disclosure relates to a combination wrench device comprising a proximal member including an elongated body extending from a proximal end to a distal end, the proximal end including a threaded shaft, the proximal member including a first recess extending from the proximal end to a first shoulder and a second recess open to the first recess and extending proximally from the first shoulder to a proximal wall, the second recess having a width smaller than a width of the first recess, the first recess configured to receive a distal portion of a first screw and the second recess configured to receive a distal portion of a second screw smaller in diameter than the first screw, and a distal member extending from a proximal end to a distal end, the proximal end being configured to be threadedly coupled over the threaded shaft of the proximal member, the distal member including a first recess extending proximally from the distal end to a first shoulder, a second recess open to the first recess and extending proximally from the first shoulder to a second shoulder, and a third recess open to the second recess and extending proximally from the second shoulder to a third shoulder, the first recess having a width larger than a diameter of the second recess and the second recess having a diameter larger than a diameter of the third recess, the first recess being configured to receive a nut therein, wherein, when the proximal and distal members are threadedly coupled, the first and second recesses of the proximal member are in open communication with the first, second and third recesses of the distal member.

The present disclosure also relates to a combination wrench system comprising a combination wrench extending from end to a distal end, comprising: a proximal member including an elongated body extending from a proximal end to a distal end, the proximal end including a threaded shaft, the proximal member including a first recess extending from the proximal end to a first shoulder and a second recess open to the first recess and extending proximally from the first shoulder to a proximal wall, the second recess having a width that is smaller than a width of the first recess, the first recess configured to receive a distal portion of a first screw and the second recess configured to receive a distal portion of a second screw smaller in diameter than the first screw, and a distal member extending from a proximal end to a distal end, the proximal end being configured to be threadedly coupled over the threaded shaft of the proximal member, the distal member including a first recess extending proximally from the distal end to a first shoulder, a second recess open to the first recess and extending proximally from the first shoulder to a second shoulder, and a third recess open to the second recess and extending proximally from the second shoulder to a third shoulder, the first recess having a width that is larger than a diameter of the second recess and the second recess having a diameter that is larger than a diameter of the third recess, the first recess being configured to receive a nut therein, wherein, when the proximal and distal members are threadedly coupled, the first and second recesses of the proximal member are in open communication with the first, second and third recesses of the distal member. The wrench system also includes a first screw, a second screw, and at least one combination clamp including a threaded shaft and a nut threadedly coupled to the shaft, the shaft and nut configured to be inserted into the distal end of the combination wrench.

BRIEF DESCRIPTION

FIG. 1 shows a side view of a combination wrench device according to a first embodiment of the present disclosure;

FIG. 2 shows a cross-sectional view of a distal portion of the combination wrench device of FIG. 1;

FIG. 3 shows a front view of the combination wrench device of FIG. 1;

FIG. 7 shows a transparent side view of a distal portion of the combination wrench device of FIG. 1 with a 6 mm Schanz screw inserted therein;

FIG. 8 shows a transparent perspective view of the distal portion of the combination wrench device of FIG. 1 with a 6 mm Schanz screw inserted therein;

FIG. 9 shows a transparent side view of a distal portion of the combination wrench device of FIG. 1 with a nut of a combination clamp inserted therein;

FIG. 10 shows a transparent perspective view of the distal portion of the combination wrench device of FIG. 1 with a nut of a combination clamp inserted therein; and FIG. 11 shows a cross-sectional view of a distal portion of the combination wrench of FIG. 1 with a drainage port.

DETAILED DESCRIPTION

Figure 4:
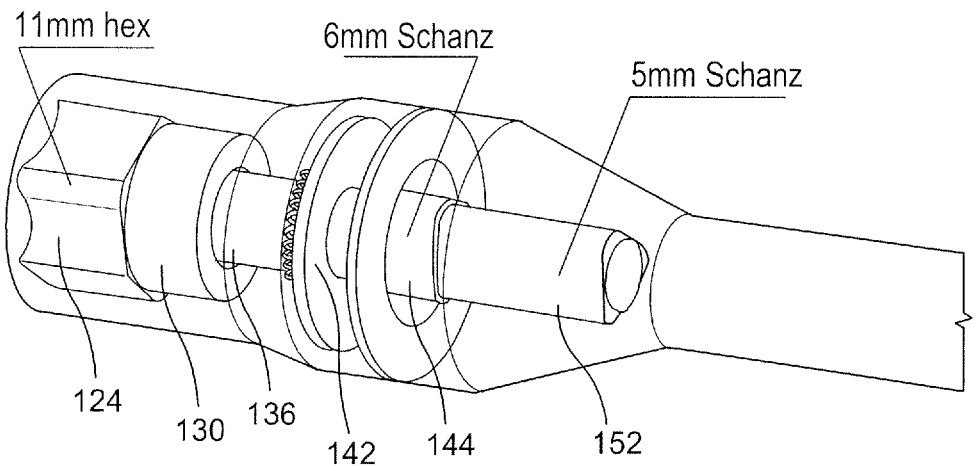
FIG. 4 shows a partially transparent view of a distal portion of the combination wrench device of FIG. 1.

The present invention may be understood with respect to the following description and the appended drawings, wherein like elements are referred to with the same reference numerals. The present invention relates to combination wrench devices which include several nested recesses for the positioning of different conventionally-sized Schanz screws and the tightening of a nut on, for example, a combination clamp. Exemplary embodiments describe a combination wrench device including nested recesses that are configured to accommodate 5 mm and 6 mm Schanz screws, as well as an 11 mm nut. Thus, by having these features nested within one combination wrench device, the user is able to adjust the insertion depths of all, for example, Synthes™ 5 mm and 6 mm Schanz screws and 11 mm nuts using a single tool. In some embodiments, the combination wrench device includes a radial spring therein to prevent the Schanz screws from falling out of the device. It should be noted that the terms "proximal" and "distal" as used herein are intended to refer to a direction toward (proximal) and away from (distal) a user of the device.

As shown in FIGS. 1-10, a combination wrench system 10 includes a combination wrench device 100, various size (e.g., 5 and 6 mm) Schanz screws 160, 162 and a combination clamp 126 including a nut 128. The combination wrench device 100, according to an exemplary embodiment, is an elongated member extending from a proximal end 102 to a distal end 104. The wrench device 100 includes a proximal handle member 106 and a distal member 108 that are coupled to one another to form the wrench device 100. As can be seen in FIG. 1, the proximal member 106 is substantially T-shaped and includes an elongated longitudinal body 110 extending from the proximal end 102 to a distal end 112 coupled to the distal member 108. The proximal member 106 also includes a cross-member 114 extending perpendicular to a longitudinal axis of the body 108 to form a T-handle. The cross-member 114 is positioned at the proximal end 102 and is configured to be gripped by the hand of the user. The proximal and distal members 106, 108, when coupled together, form a plurality of nested recesses configured to receive and retain the Schanz screws 160, 162 and nut 128 of different dimensions, as will be described in further detail below.

Figure 6:
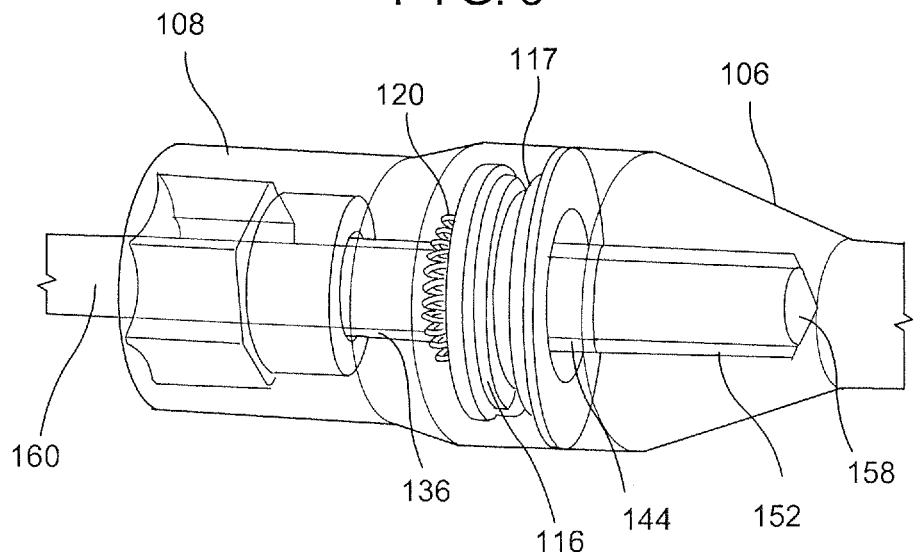
FIG. 6 shows a transparent perspective view of the distal portion of the combination wrench device of FIG. 1 with a 5 mm Schanz screw inserted therein.

In an exemplary embodiment, the proximal and distal members 106, 108 are threadedly coupled to one another, as best seen in FIG. 6. In this embodiment, the proximal member 106 includes a threaded shaft 116 at the distal end 112 configured to be received within a threaded lumen 117 at a proximal end of the distal member 108. In an exemplary embodiment, the proximal and distal members 106, 108 may be welded together at a weld seam 115 once they have been threadedly engaged. Specifically, any space between the proximal and distal members 106, 108 will be filled during the welding process. As will be described in further detail below, the proximal and distal members 106, 108, when coupled together, constrain a spring member 118 within a spring pocket 120 such that the spring member 118 provides friction to the outer surface of the Schanz screws 160, 162 when inserted into the device 100, preventing the Schanz screws 160, 162 from falling out of the distal end 104 of the device 100. The proximal and distal members 106, 108, when coupled to one another, also form an elongated channel 122 formed of a plurality of nested recesses in communication with one another with a distal end of the elongated channel 122 being open at the distal end 102 of the device 100.

As shown in FIGS. 2-4, a first recess 124 of the channel 122 extends from the distal end 102 of the device, into the distal member 108. The first recess 124, in this embodiment, is configured to receive the nut 128 present on a combination clamp 126. In an exemplary embodiment, the first recess 124 is a six-point hexagonal recess that corresponds to a six-sided 11 mm hexagonal nut 128. Thus, the first recess 124 has a width of approximately 11 mm. However, it will be understood by those skilled in the art that the first recess 124 may be sized and shaped to receive any type of nut 128, so long as the first recess 124 is greater in diameter than the Schanz screw recesses, as will be described in further detail below. The first recess 124, in this embodiment, extends from the distal end 102 to a proximal end open to a second recess 130 positioned just proximal of the first recess 124. The second recess 130 has a diameter smaller than the width of the first recess 124 such that a first shoulder 132 is formed between the first recess 124 and the second recess 130. The first shoulder 132 prevents the hex nut 128 from extending proximally past the first recess 124 and into the second recess 130.

The second recess 130, in this embodiment, is round, as depicted in FIGS. 2-4, and is configured to receive a post 134 of the combination clamp 126. Specifically, as can be seen in FIGS. 9-10, the nut 128 is threaded onto the proximal end of the post 134 of the combination clamp 126 such that a proximal portion of the post 134 extends proximally past the proximal end of the nut 128 when the nut 128 is retained on the combination clamp 126. Thus, the second recess 130 provides the space needed to receive the post 134 while the device 100 is tightening the nut 128 thereon. In an exemplary embodiment, the second recess 130 may be approximately 5 mm in length (i.e., a dimension extending along or parallel to a longitudinal axis of the device 100), extending from the first shoulder 132 to a proximal end. The second recess 130, in this embodiment, has a diameter of approximately 10.7 mm so as to accommodate a range of posts 134.

The second recess 130, as shown in FIG. 4, is open at a proximal end to a third recess 136. The third recess 136 is smaller in diameter than the second recess 130 such that a second shoulder 138 is formed between the second recess 130 and the third recess 136. The third recess 136 is substantially round and is configured to receive a portion of the Schanz screws 160, 162 therein. Thus, the third recess 136, in this embodiment, is approximately 6 mm in diameter so as to be able to receive either the 5 mm or the 6 mm Schanz screw 160, 162 therethrough. The third recess 136 extends from the second shoulder 138 to a proximal end open to the spring pocket 120. In an exemplary embodiment, the third recess 136 is approximately 4.8 mm in length and provides stability to the Schanz screw 160, 162 inserted therein.

The spring pocket 120 extends proximally from the third recess 136 and has a diameter greater than the diameter of the third recess 136 to accommodate the spring member 118 therein while also allowing the inserted Schanz screw 160, 162 to pass therethrough. A third shoulder 140 is formed between the spring pocket 120 and the third recess 136, preventing the spring member 118 from moving distally out of the spring pocket 120. The spring pocket 120 extends from the third shoulder 140 to the threaded lumen 118 positioned just proximal of the spring pocket 120. Thus, when the proximal member 106 is threadedly engaged with the distal member 108, the spring member 118 is enclosed within the spring pocket 120 with a distal surface 141 of the threaded shaft 116 preventing the spring member 118 from moving proximally out of the spring pocket 120, as will be described in further detail below. The spring pocket 120 is substantially round, conforming to the outer shape of the spring member 118. The spring member 118, in this embodiment, is a ring-shaped radial spring member 118 with a central hole 142 sized and shaped to receive the inserted Schanz screw 160, 162 therethrough. In an exemplary embodiment, the spring member 118 is at least partially radially compressed from a normal or resting state by the spring pocket 120. This radial compression of the spring member 118 prevents the spring member 118 from expanding outward so that an inward force is provided to a Schanz screw 160, 162 inserted therein, stabilizing the Schanz screw 160, 162, aiding in adjustment of the Schanz screw 160, 162, and preventing the Schanz screw 160, 162 from falling out of the distal end 104 of the device 100. In an exemplary embodiment, the spring pocket 120 may be approximately 8.65 mm in diameter. The spring member 118, in an embodiment, has a diameter slightly larger than the diameter of the spring pocket 120 when the spring member 118 is in a normal state. The diameter of the central hole 142 is approximately 5 mm so as to provide friction on the Schanz screw 160, 162 inserted therethrough. It will be understood that the spring member 118 may also be positioned in the spring pocket 120 at a normal state so long as the central hole 142 is small enough to provide friction on the Schanz screw 160, 162 inserted therethrough.

The spring pocket 120 is open at a proximal end to a fourth recess 144 extending into the proximal member 106. The fourth recess 144 is in communication with the spring pocket 120 when the proximal and distal member 106, 108 are coupled together, as shown in FIGS. 2-5. The fourth recess 144 extends through the threaded shaft 116 from the distal end 112 of the proximal member 106 to a proximal end. The fourth recess 144 is smaller than the spring pocket 120 to form a fourth shoulder 148 between the spring pocket 120 and the fourth recess 144 that prevents the spring member 118 from falling proximally out of the spring pocket 120. The fourth recess 144 in this embodiment is approximately 12 mm in length and substantially triangular in a plane extending perpendicular to the longitudinal axis of the device 100 and is configured to mate with the driving features at a distal portion of a 6 mm Schanz screw 160, 162, as shown in FIGS. 7-8. Thus, when the device 100 is rotated, torque is transmitted to the Schanz screw 160, 162 via the fourth recess 144.

The fourth recess 144 is open at a proximal end to a fifth recess 152 extending proximally therefrom. The fifth recess 152 has a width smaller than a width of the fourth recess 144 such that a fifth shoulder 156 is formed between the fourth and fifth recesses 144, 152, preventing a 6 mm Schanz screw 162 from entering the fifth recess 152. The fifth recess 152 in this embodiment is substantially triangular in a plane extending perpendicular to the longitudinal axis of the device 100. Thus, the fifth recess 152 is keyed to a triangular-shaped proximal driving feature of the 5 mm Schanz screw 160, as shown in FIGS. 9-10. The fifth recess 152 is approximately 10 mm in length so as to mate with and hold the driving features of the 5 mm Schanz screw 160 and extends to a proximal wall 158 at a proximal end of the elongated channel 122. Thus, when the device 100 is rotated, torque is transmitted to the 5 mm Schanz screw 160 via the fifth recess 152.

In an exemplary embodiment, depicted in FIG. 11, a drainage port 170 extends from a first end at first lateral side of the device 100 to a second end at a second lateral side of the device 100 along an axis perpendicular to a longitudinal axis of the device 100. The drainage port 170 is open to the fifth recess 152, as can be seen in the figured and is approximately 3 mm in diameter. The drainage port 170 aids in cleaning of the device 100 and the channel 122.

Prior to use of the device 100, the spring member 118 is inserted into the spring socket 120 of the distal member 108. Once the spring member 118 has been positioned within the spring socket 120, the threaded shaft 116 of the proximal member 106 is inserted into the threaded lumen 118 of the distal member 108 and the proximal member 106 is rotated until the distal member 108 is tightly coupled to the proximal member 106. Once coupled, the proximal and distal members 106, 108 may be permanently coupled to one another (e.g., via welding) by any conventional method.

Figure 5:
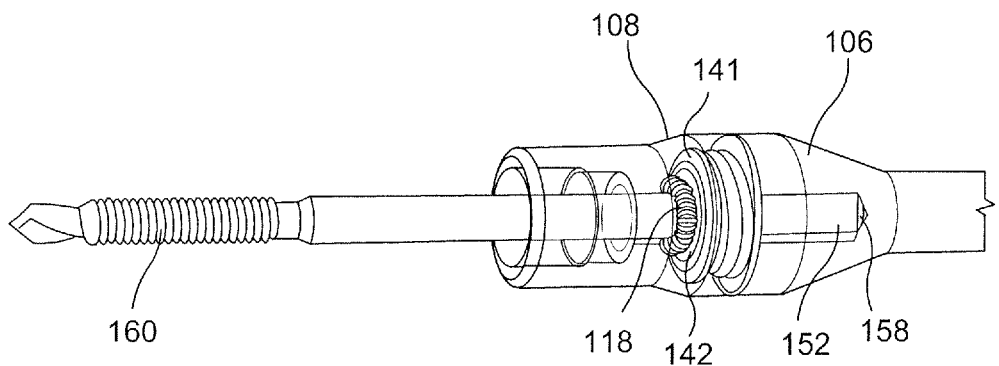
FIG. 5 shows a transparent side view of a distal portion of the combination wrench device of FIG. 1 with a 5 mm Schanz screw inserted therein.

In use, the device 100 is positioned over any one of the various screws for which it is configured (e.g., a 5 mm Schanz screw 160, as shown in FIGS. 5-6, a 6 mm Schanz screw 162, as shown in FIGS. 7-8, or an 11 mm nut 128, as shown in FIGS. 9-10). When a 5 mm Schanz screw 160 is inserted into the elongated channel 122, a proximal end 164 of the 5 mm Schanz screw 160 moves proximally through the various recesses until it hits the proximal wall 158 of the fifth recess 152. At this point, the 5 mm Schanz screw 160 is fully seated within the elongated channel 122 with the spring member 118 providing frictional force thereto to hold the Schanz screw 160 in place. The device 100 may then be rotated, transmitting torque to the 5 mm Schanz screw 160, via the keyed triangular fifth recess 152, to tighten or loosen the 5 mm Schanz screw 160. Similarly, when the 6 mm Schanz screw 162 is inserted into the elongated channel 122, a proximal end 166 of the 6 mm Schanz screw 162 moves proximally through the various recesses until it hits the fifth shoulder 156 positioned between the fourth and fifth recesses 144, 152. At this point, the 6 mm Schanz screw 162 is fully seated within the elongated channel 122 with the spring member 118 providing frictional force thereto to hold the 5 mm Schanz screw 162 in place. The device 100 may then be rotated, transmitting torque to the 5 mm Schanz screw 162, via the keyed triangular fourth recess 144, to tighten or loosen the 5 mm Schanz screw 162. The same device 100, which may be used to position the Schanz screws 160, 162 may be used to tighten the 11 mm nut 128 positioned, for example, on a combination clamp 126. When tightening the nut 128, the post 134 of the combination clamp 126, with the nut 128 positioned thereon, is inserted proximally into the elongated channel 122 until the nut 128 is seated within the first recess 124. With the nut 128 positioned in the first recess 124, the post 134 extends into the second recess 130 such that the post 134 does not interfere with the tightening of the nut 128. As described above, the first recess 124 is a hex recess keyed to the hex-shape of the nut 128 such that, when the device 100 is rotated, the first recess 124 transmits torque to the nut 128 to tighten or loosen the nut 128.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiments disclosed, but rather modifications are also covered within the scope of the present invention as defined by the appended claims.

What is claimed is:

1. A combination wrench device, comprising:
  a proximal member including an elongated body extending from a proximal end to a distal end, the proximal end including a threaded shaft, the proximal member including a first recess extending from the proximal end to a first shoulder and a second recess open to the first recess and extending proximally from the first shoulder to a proximal wall, the second recess having a width smaller than a width of the first recess, the first recess configured to receive a distal portion of a first screw and the second recess configured to receive a distal portion of a second screw smaller in diameter than the first screw; and
  a distal member extending from a proximal end to a distal end, the proximal end being configured to be threadedly coupled over the threaded shaft of the proximal member, the distal member including a first recess extending proximally from the distal end to a first shoulder, a second recess open to the first recess and extending proximally from the first shoulder to a second shoulder, and a third recess open to the second recess and extending proximally from the second shoulder to a third shoulder, the first recess having a width larger than a diameter of the second recess and the second recess having a diameter larger than a diameter of the third recess, the first recess being configured to receive a nut therein;

wherein, when the proximal and distal members are threadedly coupled, the first and second recesses of the proximal member are in open communication with the first, second and third recesses of the distal member.

2. The device of claim 1, wherein the first screw is a 6 mm Schanz screw.

3. The device of claim 1, wherein the second screw is a 5 mm Schanz screw.

4. The device of claim 1, wherein the nut is an 11 mm hexagonal nut.

5. The device of claim 4, wherein the first recess of the distal member has a hexagonal geometry that matches the outer geometry of the hexagonal nut so as to transmit torque from the distal member to the hexagonal nut.

6. The device of claim 1, wherein the distal member further comprises a spring pocket open to the third recess and extending proximally from the third shoulder to the proximal end of the distal member, the spring pocket having a diameter that is larger than the diameter of the third recess.

7. The device of claim 6, further comprising a radial spring configured to be positioned within the spring pocket, the radial spring including a central hole configured to receive one of the first and second screws therethrough, the radial spring providing an inward force on the screw to hold the screw in position within the device.

8. The device of claim 1, wherein the proximal and distal members are welded together.

9. The device of claim 1, wherein a geometry of the first and second recesses of the proximal member match a geometry of the distal portions of the first and second screws, respectively, so as to transmit torque from the proximal member to the first and second screws.

10. The device of claim 1, wherein the second recess is configured to receive a post of a combination clamp over which the nut is positioned, the post extending proximally past a proximal end of the nut.

11. The device of claim 1, wherein a diameter of the third recess is substantially equal to a width of the first recess of the proximal member, the third recess providing support to a proximal portion of one of the first and second screws inserted therethrough.

12. A combination wrench system, comprising:
a combination wrench extending from end to a distal end, comprising:
a proximal member including an elongated body extending from a proximal end to a distal end, the proximal end including a threaded shaft, the proximal member including a first recess extending from the proximal end to a first shoulder and a second recess open to the first recess and extending proximally from the first shoulder to a proximal wall, the second recess having a width that is smaller than a width of the first recess, the first recess configured to receive a distal portion of a first screw and the second recess configured to receive a distal portion of a second screw smaller in diameter than the first screw; and a distal member extending from a proximal end to a distal end, the proximal end being configured to be threadedly coupled over the threaded shaft of the proximal member, the distal member including a first recess extending proximally from the distal end to a first shoulder, a second recess open to the first recess and extending proximally from the first shoulder to a second shoulder, and a third recess open to the second recess and extending proximally from the second shoulder to a third shoulder, the first recess having a width that is larger than a diameter of the second recess and the second recess having a diameter that is larger than a diameter of the third recess, the first recess being configured to receive a nut therein, wherein, when the proximal and distal members are threadedly coupled, the first and second recesses of the proximal member are in open communication with the first, second and third recesses of the distal member;

a first screw;
a second screw; and
at least one combination clamp including a threaded shaft and a nut threadedly coupled to the shaft, the shaft and nut configured to be inserted into the distal end of the combination wrench.

13. The system of claim 12, further comprising a spring pocket open to the third recess and extending proximally from the third shoulder to the proximal end of the distal member, the spring pocket having a diameter that is larger than the diameter of the third recess.

14. The system of claim 13, further comprising a radial spring configured to be positioned within a spring pocket, the radial spring including a central hole configured to receive one of the first and second screws therethrough, the radial spring providing an inward force on the screw to hold the screw in position within the device.

15. The system of claim 12, wherein the first screw is a 6 mm Schanz screw, the second screw is a 5 mm Schanz screw and the nut is an 11 mm nut.

16. The system of claim 12, wherein a geometry of the first and second recesses of the proximal member match a geometry of the portions of the first and second screws, respectively, so as to transmit torque from the proximal member to the first and second screws.

17. The system of claim 12, wherein the first recess of the distal member has a hexagonal geometry that matches the outer geometry of the hexagonal nut so as to transmit torque from the distal member to the hexagonal nut.

18. The system of claim 12, wherein the combination wrench includes a drainage port open to the third recess, the drainage port extending from a first lateral side of the wrench to a second lateral side of the wrench along an axis perpendicular to a longitudinal axis of the wrench.

* * * * *